United States Patent [19]

Barruet et al.

[11] Patent Number: 4,777,032

[45] Date of Patent: Oct. 11, 1988

[54] PAPER DISTRIBUTING AN ACTIVE COMPOUND ON BURNING, AND A PYROTECHNIC DISTRIBUTOR USING SUCH PAPER

[75] Inventors: Patrick Barruet, Villeneuve sur Lot; Alain Fauconnier, Vert Le Petit; Pierre-Régis Carle, Cassis, all of France

[73] Assignee: Societe Nationale des Poudres et Explosifs, Paris, France

[21] Appl. No.: 896,660

[22] Filed: Aug. 14, 1986

[30] Foreign Application Priority Data

Aug. 27, 1985 [FR] France ............................... 85 12753

[51] Int. Cl.⁴ ............................................. A01N 25/20
[52] U.S. Cl. ..................................................... 424/42
[58] Field of Search ............................................ 424/42

[56] References Cited

U.S. PATENT DOCUMENTS

| 1,565,899 | 12/1925 | Bradner | 424/42 |
| 1,659,158 | 2/1928 | Oglesby et al. | 424/42 |
| 2,551,406 | 5/1951 | Yeat | 424/42 |
| 3,391,036 | 7/1968 | Bryant et al. | 424/42 |
| 4,163,038 | 7/1979 | Nishimura et al. | 424/40 |
| 4,605,549 | 8/1986 | Carle | 424/40 |

FOREIGN PATENT DOCUMENTS

| 485669 | 8/1952 | Canada | 424/42 |
| 498283 | 12/1953 | Canada | 424/42 |
| 509960 | 2/1955 | Canada | 424/42 |
| 46-19080 | 5/1971 | Japan | 424/42 |
| 53-118525 | 10/1978 | Japan | 424/42 |
| 55-108278 | 8/1980 | Japan | 424/42 |
| 58-131905 | 6/1983 | Japan | 424/42 |

OTHER PUBLICATIONS

Kirk-Othmer Encyclopedia of Chemical Technology, Third Edition, vol. 21, p. 271.
Hackhs' Chemical Dictionary, Third Edition, p. 698.
Merck Index, Ninth Edition, pp. 7740 and 7755.

*Primary Examiner*—Allen J. Robinson
*Attorney, Agent, or Firm*—Bucknam and Archer

[57] ABSTRACT

Paper distributing an active compound such as a pesticide or a lachrymatory agent, particularly intended to be used in buildings or closed enclosures.

This paper is intended to be burnt to ensure the dissemination of the active compound incorporated in the paper. To ensure an efficient and rapid dissemination by means of a large volume of combustion gas containing only a little smoke and originating from a special combustion reaction at a limited temperature so as not to decompose the active compound, this paper is a nitrocellulose-based paper in which the proportion of nitrogen is greater than 5% and in which the fibres consist of a mixture of cellulose and nitrocellulose fibres, this mixture comprising at least 18% of cellulose fibres and the active compound having a decomposition temperature above 130° C.

17 Claims, 1 Drawing Sheet

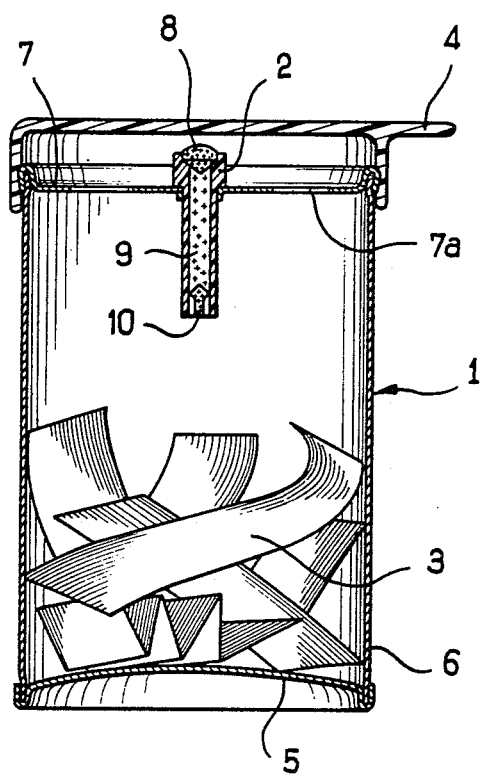

PAPER DISTRIBUTING AN ACTIVE COMPOUND ON BURNING, AND A PYROTECHNIC DISTRIBUTOR USING SUCH PAPER

The invention relates to distributing components consisting of a combustible substrate and at least one active compound such as a pesticide or a lachrymatory agent, and more particularly papers distributing active compounds of these types, which are particularly intended to be burnt in buildings, for example in premises to be disinfected or from which insects or rats are to be eliminated, or in enclosures which are at least partly closed, such as cultivation houses.

The invention also relates to fumigation devices, and more particularly to pyrotechnic distributors which make use of active compounds incorporated in a combustible substrate.

The distribution of active compounds by burning a substrate has been known for a very long time, and the use of cellulose in the form of cotton has already been described in U.S. Pat. No. 1,222,883, filed in 1915, the combustion of this cotton, distributed in candles containing gum benzoin and styrax as a base being promoted by the absorption of potassium nitrate, which makes it possible to obtain a hot flame, required for the combustion of this candle.

The introduction of organic pesticidal compounds, many of which are capable of being completely and instantly decomposed when heated to a temperature above 700° C., has very rapidly demonstrated the disadvantages of hot-flame combustion, and has led to work in two directions. The first direction consists in searching for slow and incomplete combustion which corresponds to a consumption taking place at a lower temperature but frequently producing dirty, and even irritant smoke. The second direction, which is used more widely nonadays, consists of merely heating the substrate of the active compound until the evaporation temperature of this compound is reached.

Belgian Pat. No. 644,414, which dates from 1964, mentions a consumable body for combating insects, whose combustible substrate is an organic or inorganic substance such as kaolin, silica, pumice, limestone, cardboard, paper, wood, wool or cellulose, impregnated with an inorganic oxidizing agent such as potassium, barium or lead nitrate or with chlorates, and which comprises combustion moderators such as thiourea.

French Pat. No. 2,500,265, filed in 1981 by Roussel Uclaf, also describes, by way of addition, a smoke-forming composition whose consumable substrate consists of a mixture of powdered tabu, cedar levels and pinewood comprising Brilliant Green and para-nitrophenol, such a smoke-forming composition being consumed very slowly, which makes it possible to produce cords known commercially as smoke-forming spirals or coils, whose rate of combustion may be of the order of a millimeter per minute.

Other compositions of a pyrotechnic kind are also used to distribute either pesticides or opacifiers (smoke-screen) or physiological agents (lachrymatory gases) much more quickly but, because of the higher rate of combustion, these compositions have a higher burning temperature and release more smoke. An example of such compositions is mentioned in French Pat. No. 2,456,934, which is filed by SNPE in 1979 and relates to a tear-gas grenade whose combustible substrate consists of a polymer, an inorganic oxidizing agent and additives permitting a uniform combustion.

Except for the smoke-forming spirals which are consumed very slowly, it is known that pyrotechnic combustible substrates which comprise an inorganic oxidizing agent and a combustion moderator produce too much smoke and burn at a temperature which is a little too high and, for example, French Pat. Nos. 2,378,448 and 2,382,192 give a good description of these disadvantages.

French Pat. No. 2,378,448, filed in 1978, describes one of the processes for combating harmful insects which consists in heating a moulded component made of a porous mineral substance impregnated with an active compound, by using a rising current of hot air, capable of heating this component to approximately 200°–430° C. to thus vaporize the active compound over a short period. This patent refers to a prior art for combating harmful insects, which consists of burning the combustible substrate (incineration method) in which the active compound is incorporated, and it is indicated that to improve this technique it is necessary to use a large quantity of active compound but that, despite this, since the active compound is distributed in a state in which it adheres to the particles of combustion products which are large in size, a sufficient contact between the active ingredient and the insects is not obtained and the effect produced is weak, it being moreover possible for these combustion products in the form of smoke to trigger spuriously smoke detectors installed in the buildings.

French Pat. No. 2,382,192, filed in 1978, describes another method of combating harmful insects, which also consists of indirectly heating a mixture of an active compound and a propagation agent by means of a heating element, to decompose the propagation agent thermally without causing its combustion and to volatilize the active compound. This patent contains many comparative tests based on the effect fugacity ratio of the active compounds, which is a measure of the efficiency of the distribution process and, while, according to this indirect heating process the fugacity ratios lie between 61.1% and 86.7%, comparative tests carried out when using a pyrotechnic composition comprising 30% of nitrocellulose make it possible to obtain only fugacity ratios of between 1.7% and 8.6%, demonstrating the ineffectiveness of these pyrotechnic compositions for distributing insecticides, especially of the pyrethroid group. This patent, moreover, contains a reminder that fumigation with compositions of an active chemical material and of a combustible substance which produces heat and smoke while burning is a known method, and it is stated that, in order to volatilize quickly a large quantity of the active ingredient, the combustible substance must be capable of producing a large amount of smoke. In general, however, this smoke has an irritating odour and is (highly) toxic, and it may also suggest the existence of a fire and, furthermore, the soot and other substances which it contains soil the walls, while the combustible substance itself presents a fire risk. This patent then states that the major disadvantage of known fumigation devices is that the heat of combustion of the combustible substance decomposes a proportion of the active ingredient, which is thus lost, measurements carried out using various insecticides having given volatilization ratios of less than 10%, as stated above.

The purpose of the present invention is to ensure an efficient and rapid dissemination by means of a large volume of combustion gas containing only very little smoke and originating from a special combustion reaction at a limited temperature so as not to decompose the active compound, and the invention is characterized in that, on the one hand, the paper is a nitrocellulose-based paper in which the proportion of nitrogen is greater than 5% and in that, on the other hand, the active compound has a decomposition temperature above 130° C.

More particularly, the nitrocellulose-based paper consists of a mixture of binding fibres and of nitrocellulose fibres, this mixture comprising at least 18% of connecting fibres, at least half of which are cellulose fibres. This nitrocellulose-based paper has a density of between 0.35 g/cm$^3$ and 1.3 g/cm$^3$, densities of less than 0.70 g/cm$^3$ being more effective both from the standpoint of the ability to fix the active compound and from the standpoint of combustibility at a moderate temperature, especially when this nitrocellulose-based paper is between 0.2 millimeter and 2.5 millimeters in thickness.

The nitrocellulose-based paper advantageously comprises a proportion of nitrocellulose-based fibres of between 50% and 75%, this limiting proportion of 50% being desirable to support the exothermic decomposition reaction of nitrocellulose under the majority of conditions of use, and this limiting proportion of 75% being required in the majority of cases to avoid a hot combustion which would take place at a much higher temperature and which would be unfavourable, it being possible for the proportions of nitrogen in the various nitrocellulose which are currently usable to vary from 11% to 14%.

The nitrocellulose-based papers may also comprise a resin, but when the active compound which is to be released is a pesticide, then it is highly desirable that the resin content of the nitrocellulose-based paper be less than 2% because the resins used in the paper industry, which are frequently polymers, increase the volume of smoke which is given off and impart an unpleasant irritating odour to this smoke. On the other hand, when the active compound to be released is a physiological agent such as a lachrymatory agent used by the forces for maintaining order, then there is no disadvantage in using resin contents which may range up to 6 or 8%, this much higher resin content resulting in the production of more unpleasant smoke, but still making it possible to maintain an exothermic decomposition reaction of nitrocellulose at a limited temperature.

When the nitrocellulose-based distributing paper is not used promptly after its manufacture, which is generally the case, it is then essential that this paper contains a stabilizer for nitrocellulose, a stabilizer content of 0.5 to 1.5% being adequate.

Although the invention enables satisfactory results to be obtained in all cases, and especially when the active compound is incorporated in the paper, it is preferable that this active compound be not only distributed over the paper surfaces but that, on the contrary, be distributed within the bulk of the paper itself. This arrangement permits a more homogeneous decomposition reaction of the nitrocellulose-based paper and improves the distribution of the active compound whose microcrystals or microdeposits on the paper fibres are entrained directly by the hot gases originating from the exothermic decomposition of nitrocellulose. In fact, during the work concerned with this invention it was found that nitrocellulose, which is employed in pyrotechnics because its deflagrating properties (gunpowder) and its properties of hot combustion which generates gas (propellants), was capable of decomposing thermally at a relatively low temperature of between 130° C. and 350° C. in intimate combination with cellulose fibres, provided, however, that the reaction was initiated by a suitable ignition and took place at atmospheric pressure.

More particularly, the active compound is distributed within the bulk of the nitrocellulose-based paper by impregnation in a liquid phase, the best results being produced with a liquid phase prepared from a liquid base which is not a solvent which causes nitrocellulose to gel. The individual choice of this liquid base depends on the nature of the active compound and it is preferable that this compound be soluble in the liquid base used for impregnation, the principal bases which have to be avoided because of their solvent activity which causes nitrocellulose to gel being: ether, acetone, tetrahydrofuran, dimethylformamide and cyclohexanone. The liquid base used for impregnation may be chosen especially from the group consisting of alcohols, methylene chloride, dimethyl sulphoxide, hexamethylphosphotriamide, benzene, toluene and xylene.

The nitrocellulose-based paper impregnated with active compound may be burnt in the open air, but both for reasons of convenience of safety in use and in transport, and for reasons of effectiveness in distribution, it is preferable that this paper be placed in a pyrotechnic distributor which is like a small can provided with openings and fitted with an igniting device. Under such conditions of use, the work concerned with this invention has shown that the maximum temperature reached in the centre of the distributor cannot be reduced below 200° C. and, under these conditions of use, it is then necessary for the decomposition temperature of this compound to lie above 170° C. to obtain good distribution of the active compound in the combustion gases.

The invention is more particularly adapted for the distribution of active compounds which contain one or more pesticides and especially insecticides or insect repellents, and the invention has made it possible to obtain remarkable results to ensure the distribution of insecticides belonging to the pyrethroid group, or similar, with persistent activity, and especially: deltamethrin, tralomethrin, cypermethrin, permethrin, cyfluthrin, cyhalothrin, fenfluthrin, fencythrin and fenvalerate. The efficiency of distribution of such insecticides, however, is a function of the temperatures which correspond to the onsets of the thermal decomposition exotherms, and the distribution of insecticides such as fenvalerate or tralomethrin, in which the onsets of the thermal decomposition exotherms occur at 170° C. and at 200° C. respectively does not make it possible to attain the maximum efficiency of distribution when a pyrotechnic distributor is employed.

The special combustion reaction of the nitrocellulose-based distributing paper is a self-supporting exothermic decomposition of nitrocellulose which takes place without a flame and which is accompanied by a large release of gas, the only visible part of which corresponds approximately to a large puff of cigar smoke. The formation of such a small quantity of smoke is possible only on the condition that the combustion temperature does not rise excessively, and to meet this condition it appears to be necessary for the ratio of the active compound to the weight of nitrocellulose-based paper to be less than 0.5, and this is amply sufficient to ensure the distribution of all the tested pesticides, the optimum ratio of the weight of the persistent-effect pyrethroids to the weight of the nitrocellulose-based paper being, for example, between 0.05 and 0.25.

The nitrocellulose-based distributing paper is preferably in the form of a strip, which initially makes it easier to impregnate it with the active compound in a liquid phase, it being possible for this impregnation to be carried out continuously on an industrial scale either by dipping or by a pressure roller to ensure distribution within the bulk of the paper, or by coating according to the techniques used in the paper industry for surface treatments, a simple sprinkling over one of the faces of the paper strip, coated with an adhesive beforehand, being possible but producing less effective distribution because of the absence of dispersion of the active compound between the fibres of the nitrocellulose-based paper. When the nitrocellulose-based distributing paper is used in a pyrotechnic distributor, it is advantageous for the ratio of the length to the width of the strip to lie between 3 and 10, this strip incorporating undulations or folds so as to reduce the regions of contact with the bottom of the distributor, and this makes it possible, on the one hand, to reduce heating of the walls of the distributor and, on the other hand, to approach the conditions of exothermic decomposition in open air, by avoiding any confinement due to the walls of the can.

Nitrocellulose-based distributing paper strips folded "accordeon-style" are especially suitable for pyrotechnic distributors comprising a can equipped with an igniting device and vents which permit the combustion gases containing the active compounds to leave. More particularly, the ratio of the total surface area of the vents to the internal volume of the can, expressed in self-consistent units, lies between 0.008 and 0.05, which results in a temperature rise in the centre of the distributor but, to compensate for this, makes it possible for less initial heating to be adequate to initiate the decomposition reaction of nitrocellulose without producing flames. The same operating characteristics lead to a preferential choice of the following ratios (expressed in self-consistent units such as the gram, square centimeter and cubic centimeter):

on the one hand, between the mass of nitrocellulose-based paper and the internal volume of the can, a ratio which lies between 0.005 and 0.2, and, on the other hand, a ratio of the total surface area of the vents to the mass of the nitrocellulose-based paper, a ratio which lies between 0.3 and 7.

The pyrotechnic igniting device is advantageously attached in the middle of the top of a cylindrical can and passes through this top, the frictional initiating composition being external to the can and a pyrotechnic delay providing the relay to the pyrotechnic wick which is inside the can and the lighting of which provides the heat input required to initiate the decomposition reaction of the nitrocellulose fibres closely intertwined with the cellulose fibres which are consumed.

The benefits obtained by virtue of this invention consist essentially in that it is possible to reach an exothermic reaction temperature which is sufficiently low to permit the use of the majority of the active compounds, especially pesticides, which are compounds capable of being decomposed by heat more readily than the compounds of the physiological agents which may be used, the fugacity ratios obtained for the tested active compounds being greater than 30% in all cases.

Another benefit which, while not being an essential condition for operation, is nevertheless highly advantageous, is the considerable reduction in the fumes which are given off despite the rapid dissemination of the active compounds, since it is possible, for example, to treat a 50 $m^3$ room in 10 seconds while producing only smoke resembling a puff of cigar smoke. The combination of these two benefits makes it possible, in fact, to eliminate the two major disadvantages of the fumigation processes which have been described in the state of the art in the present description, and, under these conditions, the major technical progress contributed by the present invention will make it possible to use this distribution process not only in buildings, where vaporization processes relying on electrical heating are currently employed, but also in any partly-closed buildings or enclosures such as cultivation houses which have no electricity supplies and in which the only treatments which are used at present are thermal fog-spraying of an insecticide spraying mixture through a venturi or dusting, fumigation treatments not being used despite their convenience and their speed, because the decomposition which they produce in the active compounds is much too excessive as a result of too high a combustion reaction temperature.

The invention is described in more detail in the following text with the aid of comparative experimental data and examples of implementation, and with the aid of a drawing in which the single FIGURE shows, in axial section, a cylindrical pyrotechnic distributor according to the invention, which makes use of a charge of nitrocellulose-based distributing paper.

At present, the only applications of nitrocellulose-based papers are of a military nature, since virtually all the production capacity permits the manufacture of combustible cartridges for high-calibre ammunition, the burning of this nitrocellulose-based paper taking place at a very high pressure in gun barrels. Two manufacturing processes are employed; the first process developed was the process for direct nitration of paper, which is immersed in a vat containing the sulphuric-nitric nitration mixture, and the second process, which is more recent, employs papermaking techniques, the thick pulp being spread into a sheet, drained of liquid by rolling and then dried. This second process enables the nitrogen content of the paper to be determined with great accuracy because the paper pulp is prepared by mixing binding fibres, such as pure cellulose fibres, with nitrocellulose fibres whose nitrogen content is very accurately known and, what is more, this process ensures a more homogeneous distribution of the nitrocellulose fibres in the bulk of the paper, particularly when the latter is thicker.

Many nitrocellulose-based paper formulations have been produced and, for example, the results cited in Table 1 were obtained by preparing the nitrocellulose-based pulp with, on the one hand, shredded kraft paper as a source of cellulose fibres and, on the other hand, nitrocellulose with a nitrogen content of 13.48%, the stabilizer employed being diphenylamine, and various proportions of the flocculating resin (an acrylic emulsion) being added.

TABLE 1

| Nitrocel paper | % of nitrocel. | Density ($g/cm^3$) | Mass (g) | Time (s) | Temp. (°C.) |
|---|---|---|---|---|---|
| 1 | 68 | 0.46 | 5.6 | 7 | 173 |
| 2 | 65 | 1.02 | 5.0 | 11 | 155 |
| 3 | 65 | 0.48 | 5.0 | 8 | 131 |
| 4 | 57 | 0.84 | 5.2 | 19 | 148 |
| 5 | 50 | 1.22 | 5.1 | 47 | 138 |
| 6 | 50 | 0.50 | 5 | 49 | 127 |

TABLE 1-continued

| Nitrocel paper | % of nitrocel. | Density (g/cm³) | Mass (g) | Time (s) | Temp. (°C.) |
|---|---|---|---|---|---|
| 7 | 35 | 0.38 | 5.3 | extinction | — |

In this table:
the left-hand column shows the number of the specimen of nitrocellulose-based paper,
"% of nitrocel." corresponds to the percentage of nitrocellulose,
"density" corresponds to the density of the specimen,
"mass" corresponds to the total mass ignited
"time" corresponds to the time for complete combustion and
"temp." corresponds to the temperature of flame-free decomposition of nitrocellulose within the paper.

Specimens 1, 4 and 6 contain 6% of acrylic emulsion.
Specimens 5 and 7 contain only 3% of acrylic emulsion.
Specimens 2 and 3 contain no resin.

Experiments have shown that the temperature of flame-free decomposition of nitrocellulose in the paper was virtually unchanted when the ratio of the weight of the active compound to the weight of the nitrocellulose-based paper was less than 0.2. Above this value the combustion time increases slightly and the temperature recorded tends to drop. Smoke emission is always very low but above a flocculation resin content of 2% the smoke is irritant, and the irritant effect is proportionately more pronounced the greater the mass of the specimen. This irritant effect is completely useless when pesticides such as insecticides, insect-repellents, acaricides or fungicides and the like are distributed, with the exception, however, of the distribution of chloropicrin, for example, because in this case the aim is to dislodge mammals, and especially foxes, from their lairs. In the course of tests carried out using higher resin contents it was found that the nitrocellulose-based paper itself has no insecticidal effect. On the other hand, the irritant effect of the combustion gases presents no disadvantage during the release of physiological agents such as tear gases; on the contrary, it enhances the efficiency of action of these physiological agents.

A lachrymatory nitrocellulose-based paper was prepared from the following paper formulation:
75% of nitrocellulose containing 12.7% of nitrogen
18% of inert long fibres (mixture of cellulose vegetable fibres and of synthetic polyester fibres)
6% of acrylic resin
1% of diphenylamine,
this paper, prepared so as to have a density of 0.8 g/cm³, being soaked to saturation with a liquid impregnation phase consisting of 7% of ortho-chlorobenzaldehydemalononitrile (CS) dissolved in benzene. After drying, 5 grams of lachrymatory nitrocellulose-based paper are ignited by contact with an electrically-heated resistance wire. The effect of physical discomfort is such that it is possible to enter a room approximately 20 m³ in volume only with difficulty, even after the window has been opened for 1 minute. The fugacity ratio of CS is practically 100%, since its decomposition temperature is close on 600° C., whatever the percentage of CS relative to benzene, since this percentage was varied from 0.5% to 13% in the tests which were carried out.

Tests relating to the distribution of pesticides were carried out using insecticides, which provide a wide range of thermal decomposition and are highly efficient, and especially using persistent-action pyrethroids or similar compounds. The thermal decomposition characteristics of the main insecticides tested are collated in Table 2.

TABLE 2

| Principal active compounds | Decomposition exotherms | | Percentage of compound remaining after 15 seconds' heating at T(°C.) | | | | | |
|---|---|---|---|---|---|---|---|---|
| | Beginning | End | 150° | 200° | 250° | 270° | 300° | 330° |
| Tralomethrin | 170° | 200° | — | — | 30% | 8% | — | — |
| Fenvalerate | 200° | 260° | 90% | 55% | — | 55% | — | — |
| Deltamethrin | 250° | 320° | — | — | 100% | 85% | 45% | 7% |
| Cypermethrin | 270° | 330° | — | — | — | 75% | 70% | 70% |
| Permethrin | 270° | 330° | — | — | — | 100% | 90% | 80% |

In this Table 2, the decomposition exotherms are obtained by introducing the active compounds into a high-pressure sealed cell and the rate of temperature increase is 5° C. per minute from ambient temperature. On the other hand, to study the thermal decomposition, the active compounds are merely introduced into a glass tube and are heated to the indicated temperature by means of a metal bath; after a period of 15 seconds at constant temperature, they are abruptly cooled. The time for the temperature to rise, which is not taken into account, is also 15 seconds in order to reach a temperature of 300° C. This period of 15 seconds at constant temperature is situated in the preferred range of times of combustion of the nitrocellulose-based papers shown in Table 1, which is substantially from 7 seconds to 20 seconds.

Table 2 shows that the widest variation in the percentage of insecticide which remains active when the temperature varies between 250° C. and 330° C. is shown by deltamethrin, and consequently it is when this insecticide from the group of light-stable pyrethroids is used that the biological tests are the most highly sensitive and the most searching, this sensitivity above 270° C. being responsible for some scatter in the values observed in the experiments.

Consequently, the thermal decomposition of deltamethrin was investigated in detail in order to obtain supplementary data permitting an interpretation of the tests for efficiency with various insects, and the results of this investigation are shown in Table 3.

TABLE 3

| Heating time | Maximum temperature reached | Decomposition after heating |
|---|---|---|
| 30 s | 242° C. | 10% |
| 30 s | 295° C. | 20% |
| 14 s | 309° C. | 30% |
| 5 s | 313° C. | 20% |
| 5 s | 358° C. | 77% |

To perform the various tests carried out using deltamethrin, this insecticide was dissolved in methylene chloride, which is not a solvent which gels nitrocellulose, and this liquid impregnation phase was prepared by dissolving from 0.1 to 0.2 g of deltamethrin per cubic centimeter of methylene chloride, this dosage of 100 to 200 milligrams of deltamethrin being capable of being absorbed directly within the bulk by a quantity of nitrocellulose-based paper of between 0.75 g and 2 g. Other solvents for deltamethrin which neither dissolve nor gel nitrocellulose could be used, such as benzene, xylene or HMPT. To determine with a high degree of accuracy the quantity of deltamethrin impregnating the rectangular specimens of nitrocellulose-based paper, all the depositions of the liquid impregnating phases were carried out by means of a pipette on the surface of the paper in order that the liquid phase might wet the entire surface. The liquid phase migrates virtually instantaneously throughout the thickness of the paper, especially when the thickness is less than 2.5 millimeters and when the density of the paper is less than 0.7 g/cm$^3$. A study with an electron microscope shows that deltamethrin crystallizes preferentially on the cellulose fibres and the photographs show excellent adhesion of deltamethrin to all the fibres, with the microcrystals coating these fibres and especially those of nitrocellulose. The microcrystals are more numerous in the vicinity of the faces of the nitrocellulose-based paper, but the distribution within the mass is quite homogeneous when the paper thickness is less than one millimeter, it being possible to improve the homogenization by slowing down the evaporation of methylene chloride which normally evaporats after 5 to 10 minutes' exposure in open air.

Other tests on the incorporation of active compounds in the nitrocellulose-based paper were carried out, especially by dusting onto one of the paper, glue-coated beforehand, and by coating one of the faces with a doctor blade, it being possible for this last process to be adapted to industrial scale by means of coating methods which are used for surface treatments in the paper industry, either using a doctor bade or "size-press" rolls.

Comparative tests of dissemination of active compounds were carried out by means of the pyrotechnic distributor shown in FIG. 1 in axial lengthwise section. The active part of the distributor consists of a metal can (1) which is provided with a central igniting device (2) and which contains at least one piece of distributing paper (3), and of a removable plastic lid (4) ensuring sealing during storage and transport. The metal can has a bottom (5) crimped onto the cylindrical shell (6), and when this subassembly has been filled the diffusion lid (7) is also crimped onto the top of the cylindrical shell. This diffusion lid comprises two diametrically opposed circular vents (7a) and a pyrotechnic match (2) which is attached in the middle, the frictional initiating composition (8) being external to the can. This pyrotechnic match has a pyrotechnic delay (9) of 5 seconds and a relay charge (10) consisting of a wick impregnated with black powder. The distributing paper charges which were tested were 0.5 g, 1 g, 2 g and 4 g of nitrocellulose-based paper impregnated with deltamethrin in a proportion of 50 mg, 100 mg and 200 mg per gram of nitrocellulose-based paper. The pieces of distributing papers (3) are rectangular and are placed randomly inside the can.

The pyrotechnic distributor is used by removing the plastic lid (4) and, if appropriate, clamping it onto the bottom (5) of the can (1) in the case where the distributor needs to be put on a surface which is particularly heat-sensitive. The initiating composition (8) is initiated by rubbing either on the striking surface of a matchbox or on a striking surface attached to the lid (4), and this initiating composition ignites the delay (9) which burns slowly until the wick (10) impregnated with black powder produces a considerable flow of heat towards the pieces of distributing paper, the few flames which are produced always remaining in the can and never rising up to the vents **(7*a*)**. The flow of heat generated by the igniting device initiates the exothermic decomposition reaction of nitrocellulose which is accompanied by a high release of gas and these gases, accompanied by a little smoke which may originate essentially from the combustion of the binding fibres, entrain the active compound through the vents and are rapidly disseminated throughout the enclosure in which the pyrotechnic distributor is placed.

The results of tests given hereinafter correspond to the use of a pyrotechnic distributor whose metal can is 45 millimeters in diameter and 62 millimeters in height, the diameters of the two vents being 10 millimeters.

Despite these very modest dimensions, temperature measurements carried out with a thermocouple show weak heating of the metal can, the maximum temperatures reached being substantially a function of the nitrocellulose content of the nitrocellulose-based paper, of the mass of paper placed in the distributor box and of the type of ignitor used. For example, by experimentally removing the pyrotechnic match and by using an electrically-heated wire placed temporarily in contact with the distributing paper until the exothermic decomposition reaction of nitrocellulose becomes self-supporting, the results reported in Table 4 were obtained with the use of a nitrocellulose-based paper impregnated at 100 mg per gram of inert active compound and containing 65% of nitrocellulose with a nitrogen content of 13.48% (the nitrogen content of the nitrocellulose-based paper being 8.79%).

TABLE 4

| Mass of nitrocellulose-based paper | Maximum internal temperature (after 5 to 9 seconds) |
|---|---|
| 1 gram | 220° C. |
| 2 grams | 250° C. |
| 3 grams | 300° C. |
| 4 grams | 320° C. |

Tests to determine the hot combustion thresholds of the nitrocellulose-based papers have shown that these thresholds were also a function not only of the nitrocellulose content of the nitrocellulose-based paper and of the nitrogen content of this nitrocellulose, but were also a function of the mass of paper and of the ignition heat flow characteristics. For example, when the only parameter which was changed was the content of nitrocellulose with a nitrogen content of 13.8%, and using the same pyrotechnic match and the same mass of 2 grams of nitrocellulose-based paper impregnated with deltamethrin in a proportion of 0.2 g per gram of paper, this mass of paper being placed in the distributor specified above, the maximum temperature of 300° C. was reached after 5 seconds when a nitrocellulose-based paper containing 65% of nitrocellulose was used, whereas the maximum temperature reached 410° C. after 3.2 seconds when a nitrocellulose-based paper containing 73% of nitrocellulose was used.

The following results were obtained by taking once again the same characteristics as those defined above for the nitrocellulose-based paper containing 65% of nitrocellulose and by varying the length of the wick impregnated with black powder which is situated at the end of the pyrotechnic match. With the length of the wick doubled, the temperature recorded under the same conditions changes from 300° C. to 340° C.; on the other hand, with the length of the wick shortened by one half, the recorded temperature changes from 300° C. to 250° C.

The temperatures recorded in contact with the outer surfaces of the metal can reach maximum values at the end of the emission of the gases due to the decomposition of the nitrocellulose, this emission time varying substantially from 3 seconds to 12 seconds. When the same characteristics as those defined above are adopted again, namely:

2 grams of nitrocellulose papers, 0.8 mm thick, with the following composition:
  65% of nitrocellulose fibres whose nitrogen content is 13.8%
  34% of cellulose fibres
  1% of stabilizer,
0.4 gram of active compound (pyrethroid or CS) distributed within the bulk of the paper by impregnation,
a metal can with $\phi = 45$ mm and height = 62 mm, with a pyrotechnic match whose end with the impregnated wick is situated level with the outer sheath, the maximum surface temperatures (means of the readings) obtained after 6 seconds are as follows:
  bottom: 85° C.
  shell bottom: 65° C.
  shell top: 75° C.
  lid: 105° C.

The availability of highly advantageous thermodynamic characteristics makes it possible to ensure efficient and rapid distribution of the various active compounds which may be employed, and the most search efficiency measurements have been obtained with an insecticide of the pyrethroid group which is particularly heat-sensitive: deltamethrin, which is, furthermore, one of the most efficient insecticides at the present time and whose temperature-sensitivity characteristics are shown in Tables 2 and 3 below.

Not all the deltramethrin impregnating the nitrocellulose-based paper is distributed from the pyrotechnic distributor, since analysis of the residual ash in the metal can shows that from 4 to 12% of this insecticide is left in this ash. To reduce this percentage it is necessary to raise the internal temperature in the distributor, and this appears automatically to entail a high degree of deactivation of deltamethrin and tests have shown that, to achieve a maximum actual efficiency, which corresponds to a fugacity ratio of more than 50%, there was no point in reducing the percentage of deltamethrin in the ash below 8 to 10%.

The intrinsic efficiency of deltamethrin is a function of the ambient temperature and of the ambient relative humidity, this insecticide being slightly more effective when the temperature is close to 20° C. and when relatively humidity is low. These two factors partly explain the differences observed during entomological trials, the relative sealing of the various buildings or closed enclosures being a third factor which affects the experimental results which were obtained:

in the various buildings used:

- conventional silos with a volume of less than 50 $m^3$,
- warehouses or stores capable of ranging up to 500 $m^3$,
- modern horizontal and vertical silos, up to 10 m in diameter and 60 m in height, in cultivation enclosures such as:

- "Nantes-type" tunnels 0.5 to 0.6 m in diameter and approximately fifty meters in length,
- plastic hothouses 3 m in diameter and 25 m to 100 m in length, and
- glasshouses 6 m in width and 3 m in height, with a length of 25 m.

The results obtained in a laboratory closed room (a 50-$m^3$ Peet & Grady room), at 23° C. with a constant relative humidity of 60%, have shown that the use of 0.8 g of nitrocellulose-based paper in the pyrotechnic distributor is sufficient to obtain total knockdown of the following biological indicators after 16 hours: *Musca domestica* (diptera), *Spodoptera littoralis* (caterpillars) and *Rhizopertha dominica* (*Coleopter bostrychides*). The nitrocellulose-based paper used contained 65% of nitrocellulose (13.8% of $N_2$) and the deltamethrin impregnation was only with 0.1 g per gram of nitrocellulose-based paper. Despite this low dosage of insecticide, it was found that the threshold for 50% knockdown of house flies ($KT_{50}$ for *Musca domestica*) was reached after 20 min. The same nitrocellulose-based paper, but used in a dosage of 1 g in the distributor, and impregnated with deltamethrin in a proportion of 0.2 g per gram, enabled 100% mortality of cockroaches *Periplaneta americana* to be obtained after 35 minutes.

The first tests carried out in actual cultivation structures were deliberately performed under the worst sealing conditions, whereas the laboratory tests had been performed in a hermetically closed room. These tests were carried out on the Crau plateau on a day with a violent mistral (wind from 80 to 100 km/hour) in hothouses of the plastic tunnel type, of standard manufacture, kept nonhermetically closed only for one hour after the use of the pyrotechnic distributor. The hothouses had a length of 100 m and a cross-section of a wide elliptical segment 7 m in width and 2.5 m in height. The biological indicators comprised adults of *Musca domestica* (M.d.), caterpillars (L4) of *Spodoptera littoralis* (S.l.), adults of *Acanthoscelides obtectus* (A.o. *Coleoptera bruchides*) and the adults of *Aphis craccivora* (A.c. *Cowpea aphid*). The nitrocellulose-based paper used also contained 65% of nitrocellulose (13.8% of $N_2$) and the deltamethrin (M) impregnation was with 0.1 or 0.2 g per gram of paper. The results obtained are listed in Table 5, each value shown being the mean of two or three tests carried out under each of the test conditions.

TABLE 5

| Pyrotechnic distributors | | | | | | |
|---|---|---|---|---|---|---|
| M dosage | M paper | No. of cans | Knockdown rate after 1 hour M.d. | S.l. | A.o. | A.C. |
| 0,1 g/g | 1 g | 5 | 100% | 90% | 30% | 100% |
| 0,1 g/g | 1 g | 3 | 80% | 80% | 50% | 100% |
| 0,2 g/g | 2 g | 3 | 98% | 90% | 45% | 100% |
| 0,1 g/g | 3 g | 2 | 95% | 70% | 55% | 90% |
| 0,2 g/g | 3 g | 2 | 90% | 85% | 60% | 100% | distributed uniformly along the greenhouse and were ignited simultaneously. The periods for which the greenhouses are closed for treatment are generally from 8 hours to 12 hours, and the knockdown rate after 1 hour is therefore merely an indication of efficiency which is of great interest but which does not correspond to actual knockdown rates (except for the 100% rate) which may be obtained with normal periods of closure and a weak wind, the absence of wind being undesirable especially when the distributors are at some distance from each other. For example, the complete destruction of caterpillars of Spodoptera littoralis was obtained over periods from 3 h 30 to 5 h in the same plastic greenhouse on days with a weak wind and without wind, by arranging 3 distributors, each containing 4 grams of nitrocellulose-based paper impregnated with deltamethrin in a proportion of 0.05 g per gram of paper. The knockdown rate for Aleurodes (Hemiptera) in greenhouses of the plastic tunnel type remains less satisfactory at present, but the only tests which were carried out involved distributors whose fugacity ratio was only 45%. Other tests performed in the laboratory closed room have enabled knockdown rates of 80% and even 98% to be attained after a contact time from 4 hours to 15 hours.

Other tests were carried out to measure the efficiency of distribution of insecticides over insects of stored foodstuffs, and three Coleoptera curculionides were chosen:

Sitophilus granarius (S.g.), which attacks chiefly wheat,

Sitophilus oryzae (S.o.) which attacks chiefly rice, and

Tribolium castaneum (T.c.) which attacks chiefly flour.

The tests took place in the 50 m$^3$ laboratory closed room, which is hermetic, and this corresponds substantially to actual conditions, since silos or warehouses are quite well sealed. The three species of weevils were arranged in various manners:

in direct contact with the atmosphere of the room,
in indirect contact, the insects being capable of withdrawing from the treated atmosphere by burrowing into a 2 cm layer of wheat, rice or flour, and in a hidden position under a polystyrene box the base of which was pierced with holes enabling the insects to pass.

In the case of the tests carried out with deltamethrin, these tests permitting a more direct comparison with the described preceding tests, a single pyrotechnic distributor was placed on the floor in the room, and the results listed in Table 6, for example, were obtained using only one gram of nitrocellulose-based paper impregnated either with 0.2 g of deltamethrin (M) or with 0.1 g, the test contact times being 4 hours and 16 hours, and monitoring being carried out either 4 hours or 7 days after the contact time.

TABLE 6

| | | Percentages of mortality | | | | |
|---|---|---|---|---|---|---|
| | | 0,2 g of ΔM | | | | 0,1 g of ΔM |
| | | 4-hour contacts monitoring | | 16-hour contacts monitoring | | |
| Conditions | Insects | 4 h | 7 d | 4 h | 7 d | 4 h |
| Direct contact on the ground | Sg | 100 | 100 | 100 | 100 | 100 |
| | So | 50 | 60 | 100 | 100 | 100 |
| | Tc | 100 | 100 | 100 | 100 | 100 |
| Direct contact at 2 m height | Sg | 100 | 100 | 100 | 100 | 100 |
| | So | 100 | 100 | 100 | 100 | 100 |
| | Tc | 90 | 95 | 100 | 100 | 96 |
| Indirect contact on the ground | Sg | 100 | 100 | 92 | 92 | 90 |
| | So | 40 | 45 | 36 | 28 | 80 |
| | Tc | 16 | 16 | 95 | 25 | 48 |
| Indirect contact | Sg | 100 | 100 | 100 | 70 | 95 |
| | So | 100 | 100 | 100 | 80 | 90 |

TABLE 6-continued

| | | Percentages of mortality | | | | |
|---|---|---|---|---|---|---|
| | | 0,2 g of ΔM | | | | 0,1 g of ΔM |
| | | 4-hour contacts monitoring | | 16-hour contacts monitoring | | |
| Conditions | Insects | 4 h | 7 d | 4 h | 7 d | 4 h |
| | Tc | 20 | 15 | 85 | 20 | 25 |
| Hidden position | Sg | 100 | 100 | 95 | 100 | — |
| | So | 100 | 100 | 95 | 100 | — |
| | Tc | 98 | 98 | 98 | 80 | |

We claim:

1. A composition capable of disseminating an effective amount of an insecticide, an insect repellant or a lachrymatory agent which consists of (1) a combustible substrate and (2) said insecticide, insect repellant or lachrymatory agent; said combustible substrate is paper consisting essentially of a mixture of binding fibers and 50-75% nitrocellulose fibers, said paper having nitrogen content greater than 5%, said insecticide, insect repellant or lachrymatory agent having a decomposition temperature above 130° C.

2. The composition according to claim 1 wherein said insecticide, insect repellant or lachrymatory agent is distributed within the bulk of said paper.

3. The composition according to claim 1 wherein said insecticide, insect repellant or lachrymatory agent is distributed within the bulk of the paper by impregnation in a liquid phase, said liquid phase being made from a liquid base which is not a solvent capable of gelling nitrocellulose, wherein said insecticide, insect repellant or lachrymatory agent is soluble in said liquid impregnation base.

4. The composition according to claim 1 wherein the ratio of the weight of said insecticide, insect repellant or lachrymatory agent to the weight of said paper is between 0.05 and 0.5.

5. The composition according to claim 1 wherein said insecticide, insect repellant or lachrymatory agent has a decomposition temperature above 170° C. of bonding fibers which are a mixture of cellulose fibers and synthetic polyester fibers, 6% by weight acrylic resin, 1% by weight diphenylamine and 7% of the lachrymator agent orthochlorobenzaldehydemalononitrile.

6. The composition according to claim 1 wherein said paper additionally contains up to 2% of a flocculating resin.

7. The composition according to claim 1 wherein said paper comprises at least 18% of binding fibers and at least one half of said binding fibers are cellulose fibers.

8. The composition according to claim 1 wherein said paper has a density between 0.35 g/cm$^3$ and 1.3 g/cm$^3$.

9. The composition according to claim 8 wherein the thickness of the paper is between 0.2 millimeter and 2.5 millimeter.

10. The composition according to claim 9 wherein the paper comprises 0.5-1.5% of a stabilizer for nitrocellulose.

11. The composition according to claim 3 wherein said liquid base is a member selected from the group consisting of alcohols, methylene chloride, dimethyl sulfoxide, hexamethylphosphotriamide, benzene, toluene and xylene.

12. The composition according to claim 1 wherein said paper is in the form of a strip.

13. The composition according to claim 1 wherein said insecticide is a member of the pyrethroid group.

14. The composition according to claim 1 wherein said insecticide is deltamethrin, tralomethrin, cypermethrin, permethrin, cyfluthrin, cyhalothrin, fenfluthrin, fencythrin or fenvalerate.

15. The composition according to claim 13 wherein the ratio of the weight of the pyrethroid to the weight of said paper is between 0.05 and 0.25.

16. The composition according to claim 1 wherein the nitrogen content of said nitrocellulose is 11–14% by weight.

17. A lachrymatory composition comprising 75% by weight nitrocellulose containing 12.7% nitrogen, 18% by weight of bonding fibers which are a mixture of cellulose fibers and synthetic polyester fibers, 6% by weight acrylic resin, 1% by weight diphenylamine and 7% of the lachrymator agent orthochlorobenzaldehydemalononitrile.

* * * * *